(12) United States Patent
Chan

(10) Patent No.: US 8,553,076 B2
(45) Date of Patent: Oct. 8, 2013

(54) CONTACT MEASURING ENDOSCOPE APPARATUS

(75) Inventor: Chih-Chun Chan, Miaoli County (TW)

(73) Assignee: Medical Intubation Technology Corporation, Taoyuan Hsien (TW)

( * ) Notice: Subject to any disclaimer, the term of this patent is extended or adjusted under 35 U.S.C. 154(b) by 595 days.

(21) Appl. No.: 12/456,774

(22) Filed: Jun. 23, 2009

(65) Prior Publication Data

US 2010/0201796 A1   Aug. 12, 2010

(30) Foreign Application Priority Data

Feb. 6, 2009 (TW) ............................... 98103980 A

(51) Int. Cl.
*A61B 1/04* (2006.01)
*A61B 5/00* (2006.01)
*A61B 1/00* (2006.01)

(52) U.S. Cl.
USPC ............................... 348/68; 600/309; 600/117

(58) Field of Classification Search
USPC .......................................................... 348/68
See application file for complete search history.

(56) References Cited

U.S. PATENT DOCUMENTS

| 5,967,968 A * | 10/1999 | Nishioka | 600/117 |
| 2001/0051766 A1 * | 12/2001 | Gazdzinski | 600/309 |
| 2002/0166946 A1 * | 11/2002 | Iizuka et al. | 250/201.2 |

* cited by examiner

*Primary Examiner* — Christopher S Kelley
*Assistant Examiner* — Hee-Yong Kim
(74) *Attorney, Agent, or Firm* — Hudak, Shunk & Farine Co. LPA

(57) ABSTRACT

A contact measuring endoscope apparatus includes a case located at a front end of the apparatus to define a accommodating space; a contact probe connected to and projected from an end of the case by a fixed distance; a light emitting element for emitting light; an image pickup lens arranged in the accommodating space for gathering light reflected from an external object to be measured, so as to form an optical image; a light sensor arranged in the accommodating space to locate adjacent to one side of the image pickup lens for converting the optical image into a digital image; and a measuring module. When the contact probe is caused to contact the object to be measured, a fixed distance between the image pickup lens and the object can be maintained and therefore the digital image can be in the fixed scale.

13 Claims, 4 Drawing Sheets

CONTACT MEASURING ENDOSCOPE APPARATUS

FIELD OF THE INVENTION

The present invention relates to an endoscope apparatus, and more particularly to an endoscope apparatus for measuring an object by contacting with the object.

BACKGROUND OF THE INVENTION

Size measuring is a highly popularized technique in medical and industrial fields for measuring sizes and profiles of different areas, organs of a human body, or any object or workpiece in an external environment. Among others, a non-contact measuring endoscope is a currently frequently adopted measuring apparatus. The non-contact measuring endoscope employs light reflection principle and triangulation to irradiate light emitted from a light emitting element onto an object to be measured. The light is then reflected from the object onto two to four light sensors located at different positions. After receiving the reflected light, these light sensors respectively produce an image, so that there are two to four images being formed. These images are compared to obtain size data of the actual image. The non-contact measuring with an endoscope provides measurements much precise than that of conventional contact measuring, and has therefore become a high-level detection method. However, the non-contact measuring endoscope is quite expensive. In the event users only need a measuring apparatus with a generally acceptable precision instead of a high-precision measuring apparatus, they surely would not have the intention to purchase the expensive measuring apparatus. Thus, the high-level non-contact measuring endoscope apparatus gradually loses its competing capability in the market.

To overcome the problems of prior art, the inventor based on the research and practical experience has developed a contact measuring endoscope to annihilate the above shortcomings with practical method.

SUMMARY OF THE INVENTION

A primary object of the present invention is to provide a contact measuring endoscope apparatus that is able to get an optical image of the fixed scale by contacting an object to be measured with a contact probe and gathering light reflected from the object.

Another object of the present invention is to provide a contact measuring endoscope apparatus that uses a light sensor to convert the optical image of the fixed scale into a digital image of the fixed scale, and then uses a measuring module to measure and obtain sizes of different parts on the image.

To achieve the above and other objects, the contact measuring endoscope apparatus according to the present invention includes a case, a contact probe, a light emitting element, an image pickup lens, a light sensor, and a measuring module. The case is located at a front end of the contact measuring endoscope apparatus to define a accommodating space therein. The contact probe is connected to and projected from an end of the case. The light emitting element emits light. The image pickup lens is arranged in the accommodating space for gathering light reflected from an external object, so as to form an optical image. The light sensor is arranged in the accommodating space to locate adjacent to one side of the image pickup lens for converting the optical image into a digital image. The contact probe has a predetermined fixed length. When the contact probe is caused to contact the object, a fixed distance between the image pickup lens and the object can be maintained; and when the light is reflected on the image pickup lens and reaches at the light sensor, the digital image is in the fixed scale. Thereafter, the measuring module measures the digital image of the fixed scale to obtain one or all of lengths, widths and areas of different parts on the digital image.

With the above arrangements, the contact measuring endoscope apparatus of the present invention provides one or more of the following advantages:

(1) The contact measuring endoscope apparatus has a contact probe for touching an object, and a measuring module capable of computing to obtain sizes of an image, so that the high cost for purchasing a non-contact measuring endoscope apparatus can be largely reduced; and (2) The contact measuring endoscope apparatus uses a simple-structured contact probe and a measuring module capable of computing to obtain sizes of an image, so that maintenance of the apparatus can be largely reduced while the usable life of the apparatus can be extended.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Figure 1:
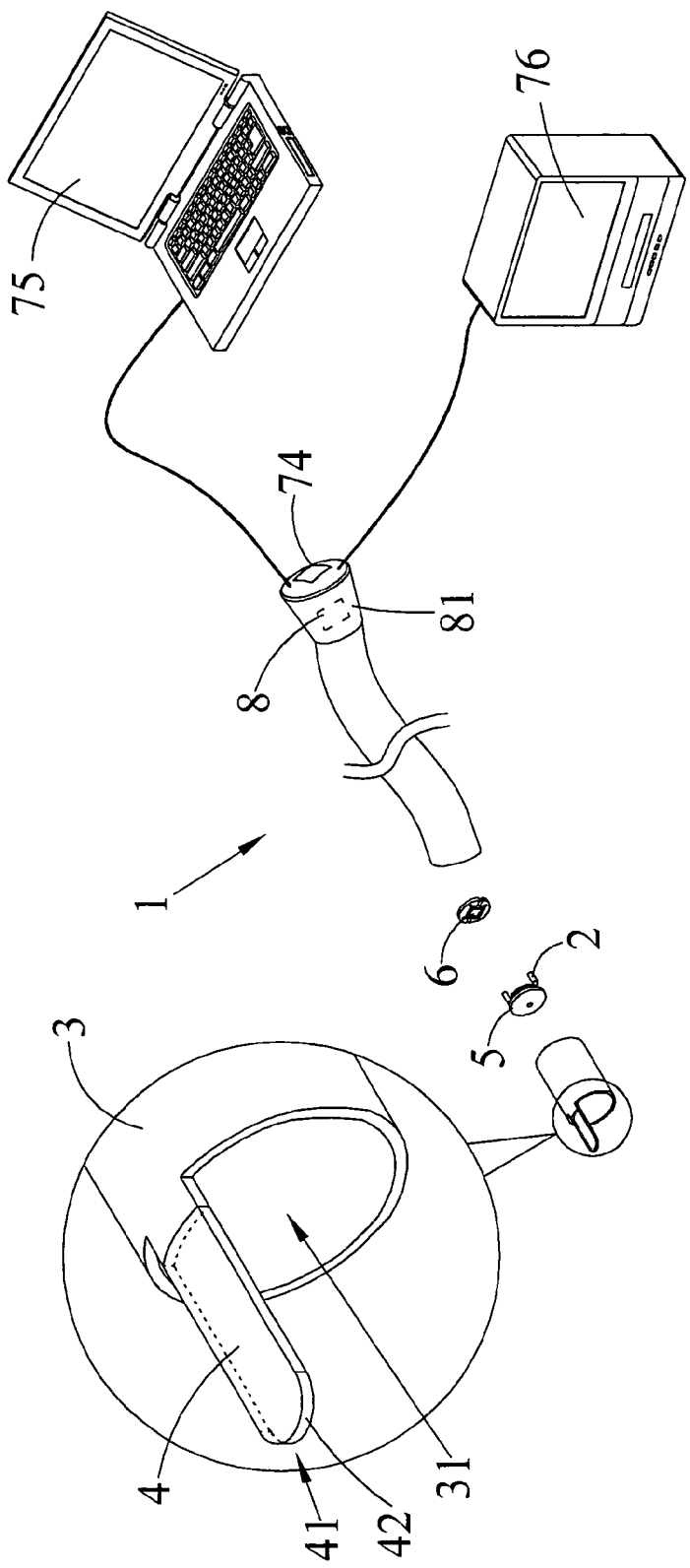
FIG. 1 is an exploded perspective view of a contact measuring endoscope apparatus according to a first preferred embodiment of the present invention.

The present invention will now be described with some preferred embodiments thereof. For the purpose of easy to understand, elements that are the same in the preferred embodiments are denoted by the same reference numerals.

Please refer to FIG. 1 that is an exploded perspective view of a contact measuring endoscope apparatus 1 according to a first preferred embodiment of the present invention, which is a multipurpose measuring endoscope apparatus for use in industrial and medical fields. As shown, the contact measuring endoscope apparatus 1 includes a case 3, a contact probe 4, a light-emitting element 2, an image pickup lens 5, and a light sensor 6.

The case 3 can be made of a metal material, a metal alloy material, a plastic material, or a ceramic material, and is located at a front end of the contact measuring endoscope apparatus 1 to define a accommodating space 31 therein.

Figure 2:
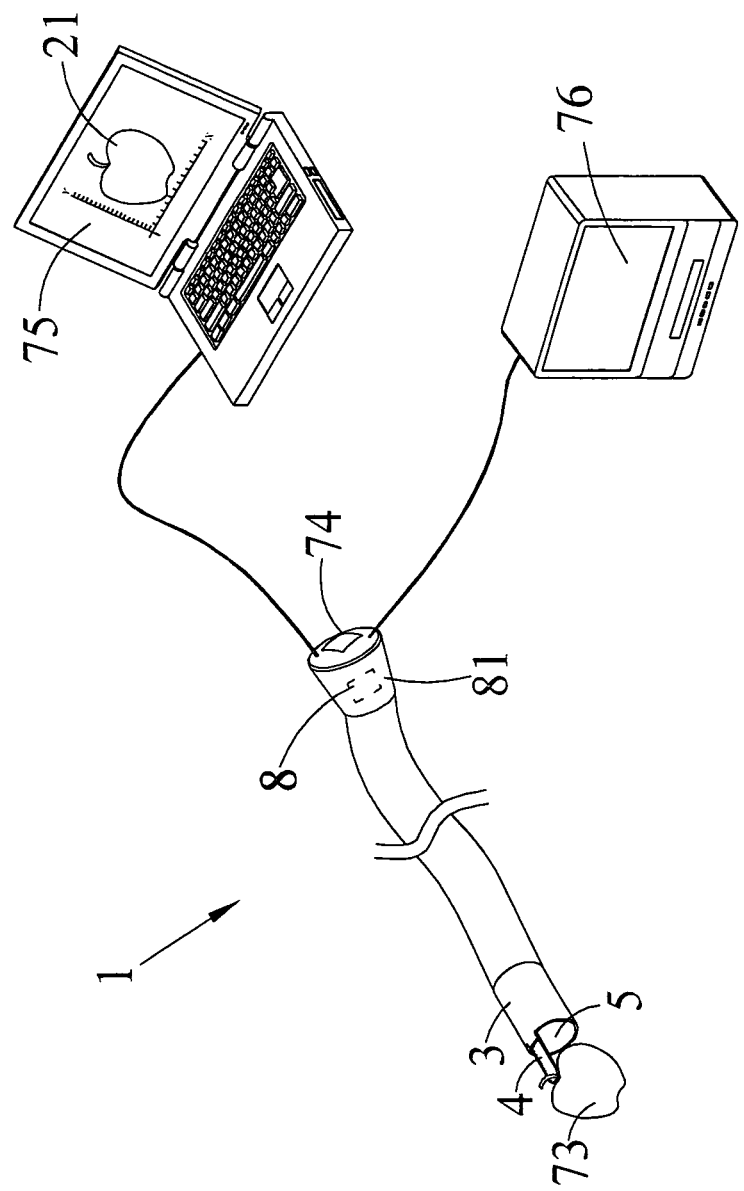
FIG. 2 is a perspective view showing the operation of the contact measuring endoscope apparatus according to the first preferred embodiment of the present invention.
Figure 3:
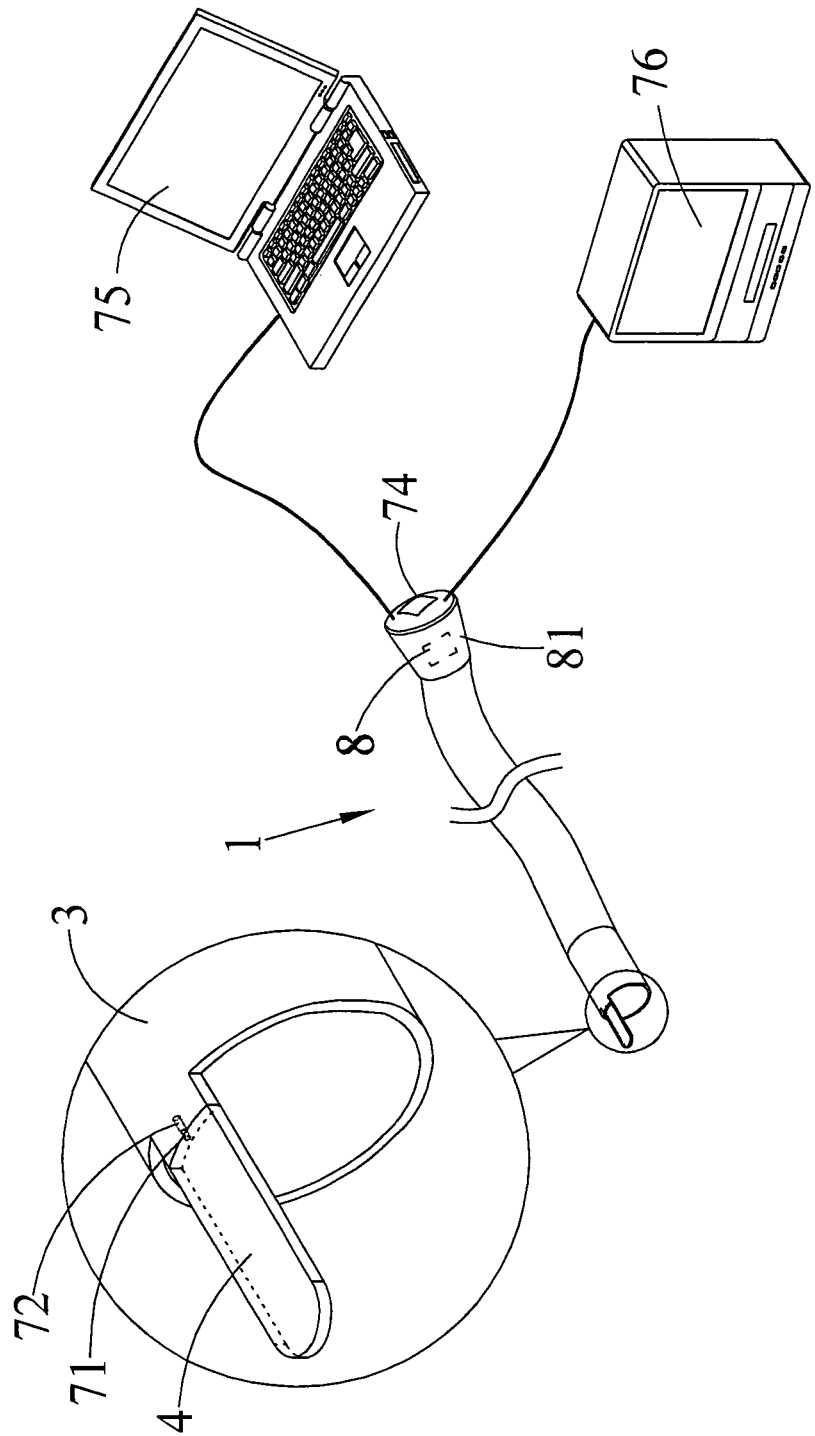
FIG. 3 is an assembled perspective view of a contact measuring endoscope apparatus according to a second preferred embodiment of the present invention.
Figure 4:
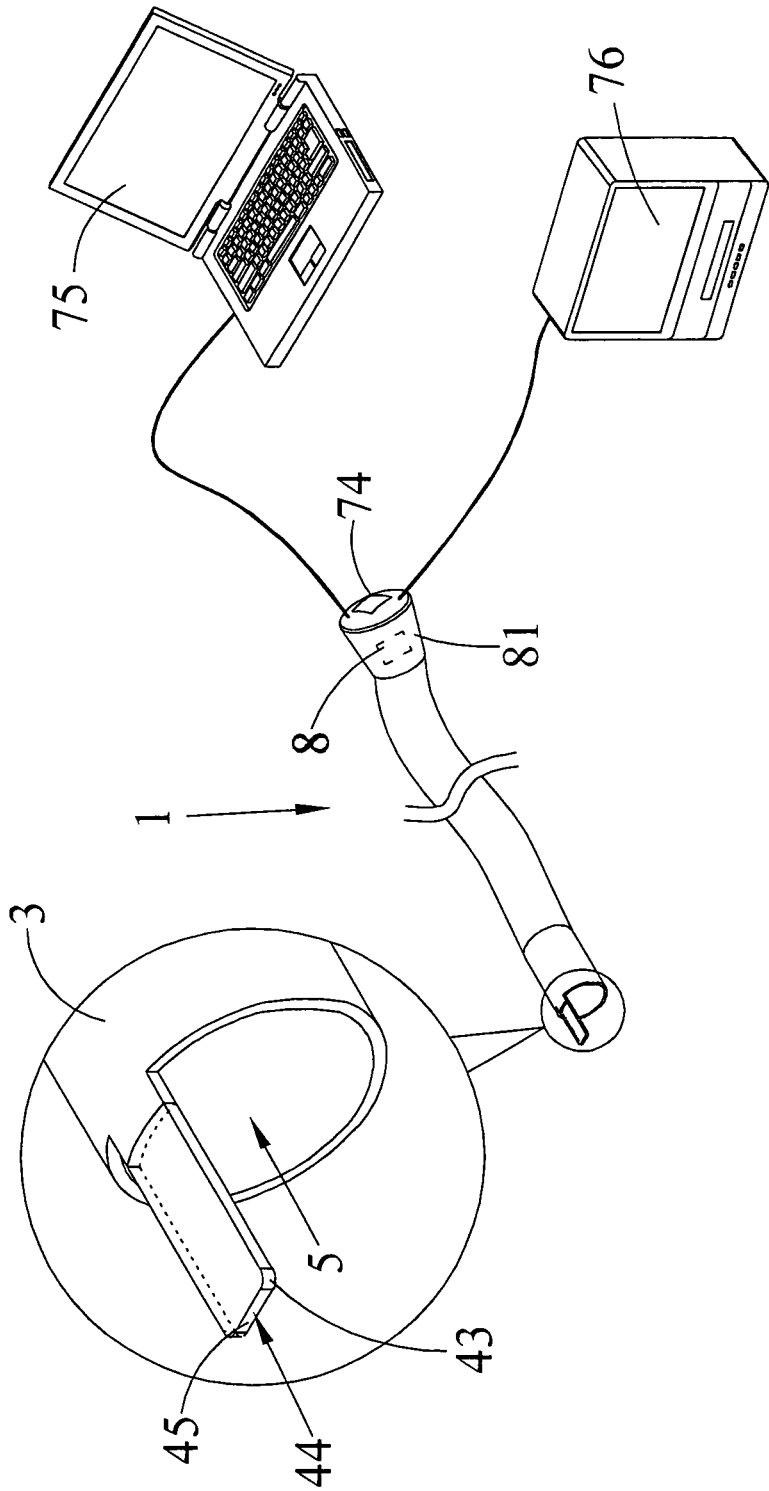
FIG. 4 is an assembled perspective view of a contact measuring endoscope apparatus according to a third preferred embodiment of the present invention.

The contact probe 4 is connected to and forward projected from an end of the case 3 to axially extend therefrom. The contact probe 4 can be connected to the case 3 in different manners without specific limitation. For example, the contact probe 4 can be integrally connected to the case 3, mechanically screwed to the case 3 through engagement of a bolt 71 with an internally threaded hole 72, as shown in FIG. 3, or assembled at an end of the case 3. The contact probe 4 is in the form of a flat plate. An end of the contact probe 4 can have a curved end 41 to define a smooth curved end surface 42. Alternatively, the end of the contact probe 4 can have a straight end 43 to define a smooth flat end surface 44, as shown in FIG. 4. The use of a contact probe 4 with a smooth curved end surface 42 or a smooth flat end surface 44 can protect an object 73 against undesirable damage, as shown in FIG. 2. The object 73 can be different areas or various organs of human body, or any other object in an external environment. In the illustrated first preferred embodiment, the contact probe 4 is integrally connected to an end of the case 3, and has a curved end 41 to define a smooth curved end surface 42. However, it is understood the contact probe 4 is not limited to the above described connection manner and end surface.

The contact probe 4 can be made of a metal material, a metal alloy material, a plastic material, or a ceramic material. In the illustrated first preferred embodiment, the contact probe 4 is made of a material the same as that for the case 3. Again, it is understood the contact probe 4 can be made of other suitable materials without being limited to the material being used to make the case 3.

The light emitting element 2 is used to emit light, and can be a light emitting diode (LED) or any other element capable of emitting light. The light emitting element 2 can be mounted on the contact measuring endoscope apparatus 1 at any position thereof, such as at a front portion, a middle portion, or a rear portion of the contact measuring endoscope apparatus 1, or in the accommodating space 31 in front of the contact measuring endoscope apparatus 1. When the light emitting element 2 is mounted at the middle or the rear portion of the contact measuring endoscope apparatus 1, an optical fiber can be used to transmit light, so that light from the light emitting element 2 can still be emitted at the front end of the contact measuring endoscope apparatus 1. In the illustrated first preferred embodiment, the light emitting element 2 is arranged on an outer periphery of the image pickup lens 5.

The image pickup lens 5 is a light-transmittable lens, and can be made of a glass material, an acrylic material, or a plastic material. The image pickup lens 5 is located in the accommodating space 31 for gathering light reflected from an object 73 to form an optical image.

The light sensor 6 is arranged in the accommodating space 31 adjacent to one side of the image pickup lens 5 for converting the optical image into a digital image 21. The light sensor 6 can be a charge-coupled device (CCD), a photoelectric diode for a complementary metal-oxide-semiconductor (CMOS), or any other light sensor that is able to convert the optical image into the digital image.

The contact measuring endoscope apparatus 1 further includes a measuring module 8 and a processing system 81 for analyzing and measuring a digital image of the fixed scale, so as to obtain all or one of the lengths, widths and areas of the digital image 21 at different parts thereof. The measuring module 8 is a software program being installed on the processing system 81 in the contact measuring endoscope apparatus 1, or on an external processing system, such as a processing system in a computer.

Please refer to FIG. 2 that shows the operation of the contact measuring endoscope apparatus 1 according to the first preferred embodiment of the present invention. As shown, the contact probe 4 having a predetermined fixed length is caused to contact an object 73. In the illustrated embodiment, the object 73 is an apple. Light emitted from the light emitting element 2 irradiates on the object 73 and is reflected on the image pickup lens 5 and reaches at the light sensor 6. Since the contact probe 4 has a fixed length, a fixed distance can be maintained between the object 73 and the image pickup lens 5, and the digital image and the optical image 21 can be in the fixed scale. Thereafter, the measuring module 8 analyzes and measures the digital image 21 of the fixed scale to obtain the lengths, widths and areas of different parts of the digital image 21. Finally, the obtained measurements are output to a first display 74, a second display 75, or a third display 76.

FIG. 3 is an assembled perspective view of a contact measuring endoscope apparatus 1 according to a second preferred embodiment of the present invention. The second embodiment is generally structurally and functionally similar to the first embodiment, except that the contact probe 4 thereof is connected to the case 3 in a manner different from that in the first embodiment. In the second embodiment, the contact probe 4 is provided with a bolt 71 and the case 3 is correspondingly provided with an internally threaded hole 72; and the contact probe 4 is connected to and projected from an end of the case 3 by screwing the bolt 71 into the threaded hole 72. Alternatively, the contact probe 4 can be provided with an internally threaded hole for meshing with a bolt provided on one end of the case 3. In either way, the contact probe 4 in the second embodiment is mechanically screwed to the case 3, which is different from the integral connection of the contact probe 4 to the case 3 as the case in the first embodiment.

FIG. 4 is an assembled perspective view of a contact measuring endoscope apparatus 1 according to a third preferred embodiment of the present invention. The third embodiment is generally structurally and functionally similar to the first embodiment, except that the contact probe 4 thereof has a shape different from that of the contact probe 4 in the first embodiment. In the third embodiment, the contact probe 4 has a straight end 43 to define a smooth flat end surface 44 with two rounded corners 45. With the contact probe 4 having a smooth flat end surface 44, the external object 73 to be measured is protected against undesirable damage by the contact probe 4. In brief, the contact probe 4 in the third embodiment has a straight end 43 and a smooth flat end surface 44, which are different from the curved end 41 and the smooth curved end surface 42 of the contact probe 4 in the first embodiment.

The present invention has been described with some preferred embodiments thereof and it is understood that many changes and modifications in the described embodiments can be carried out without departing from the scope and the spirit of the invention that is intended to be limited only by the appended claims.

What is claimed is:

1. A contact measuring endoscope apparatus, comprising:
   a case being located at a front end of the contact measuring endoscope apparatus to define a accommodating space therein;
   a contact probe being integrally connected to and forward projected from an end of the case;
   a light emitting element being capable of emitting light therefrom;
   an image pickup lens being arranged in the accommodating space of the case for gathering the light emitted from the light emitting element, irradiated on and then reflected from an external object, so as to form an optical image;
   a light sensor being arranged in the accommodating space of the case to locate adjacent to one side of the image pickup lens for converting the optical image into a digital image; and a measuring module for measuring the digital image of a fixed scale, so as to accordingly obtain at least one of the lengths, widths and areas of different parts of the digital image;

wherein the contact probe having a predetermined fixed length is caused to contact the object, so that a fixed distance between the image pickup lens and the object can be maintained and therefore the digital image is in the fixed scale.

2. The contact measuring endoscope apparatus as claimed in claim 1, wherein the measuring module is a software program.

3. The contact measuring endoscope apparatus as claimed in claim 1, wherein the light emitting element is a light emitting diode (LED).

4. The contact measuring endoscope apparatus as claimed in claim 1, wherein the light sensor is selected from a group consisting of a charge-coupled device (CCD) and a photoelectrical diode for a complementary metal-oxide- semiconductor (CMOS).

5. The contact measuring endoscope apparatus as claimed in claim 1, wherein the image pickup lens is a light-transmittable lens.

6. The contact measuring endoscope apparatus as claimed in claim 5, wherein the light-transmittable lens is selected from a group consisting of a glass lens, an acrylic lens, and a plastic lens.

7. The contact measuring endoscope apparatus as claimed in claim 1, wherein the case is made of a material selected from a group consisting of a metal material, a metal alloy material, a plastic material, and a ceramic material.

8. The contact measuring endoscope apparatus as claimed in claim 1, wherein the contact probe is made of a material selected from a group consisting of a metal material, a metal alloy material, a plastic material, and a ceramic material.

9. The contact measuring endoscope apparatus as claimed in claim 7, wherein the contact probe is made of a material the same as that for the case.

10. The contact measuring endoscope apparatus as claimed in claim 1, wherein the contact probe has a curved end to define a smooth curved end surface.

11. The contact measuring endoscope apparatus as claimed in claim 1, wherein the contact probe has a straight end to define a smooth flat end surface.

12. The contact measuring endoscope apparatus as claimed in claim 1, wherein the object to be measured can be different areas, organs of a human body or an object in an external environment.

13. The contact measuring endoscope apparatus as claimed in claim 1, wherein the light emitting element is arranged on an outer periphery of the image pickup lens.

* * * * *